United States Patent [19]
Saffer

[11] Patent Number: 4,663,774
[45] Date of Patent: May 5, 1987

[54] X-RAY DIAGNOSTICS INSTALLATION WITH ROTATABLE SUPPORT PLATE

[75] Inventor: Edmund Saffer, Eggolsheim, Fed. Rep. of Germany

[73] Assignee: Siemens Aktiengesellschaft, Berlin and Munich, Fed. Rep. of Germany

[21] Appl. No.: 693,054

[22] Filed: Jan. 22, 1985

[30] Foreign Application Priority Data

Feb. 28, 1984 [DE] Fed. Rep. of Germany ....... 3407221

[51] Int. Cl.⁴ .............................................. G21K 1/00
[52] U.S. Cl. .................................... 378/154; 378/37; 378/167; 378/181
[58] Field of Search ............... 378/154, 179, 185–187, 378/167, 181, 37, 97; 248/181–182, 288.3

[56] References Cited

U.S. PATENT DOCUMENTS 1,646,065 10/1927 Pohlmann ............................ 378/181
2,720,595 10/1955 Goldfield et al. ..................... 378/97
3,251,570 5/1966 Frost et al. ........................... 248/181
3,747,884 7/1973 Steisslinger et al. ................. 248/181
4,060,733 11/1977 Franke et al. ......................... 378/97
4,132,897 1/1979 Ohlson et al. ....................... 378/167
4,286,157 8/1981 Eickel et al. .......................... 378/37

Primary Examiner—Craig E. Church
Assistant Examiner—John C. Freeman
Attorney, Agent, or Firm—Hill, Van Santen, Steadman & Simpson

[57] ABSTRACT

An X-ray diagnostics installation has an X-ray tube for directing an X-ray beam at an examination subject disposed within the beam path on a support plate, the support plate having a secondary radiation grid on one side thereof, and having a receptacle therein for an X-ray film cassette. The support plate is mounted so as to be rotatable about an axis which is perpendicular to a central ray of the X-ray beam such that the secondary radiation grid can be optionally disposed in front of or behind the X-ray film cassette as viewed in the radiation direction, while the film focus distance remains the same.

10 Claims, 5 Drawing Figures

X-RAY DIAGNOSTICS INSTALLATION WITH ROTATABLE SUPPORT PLATE

BACKGROUND OF THE INVENTION

1. Field of the Invention

The present invention relates to X-ray diagnostics installations, and in particular to a support plate for an examination subject for such an installation.

2. Description of the Prior Art

X-ray diagnostic installations are known for the production of mammography exposures having a support plate for supporting the patient's breast, the support plate having a receptacle chamber for receiving an X-ray film cassette, and a secondary radiation grid overlying the receptacle such that the grid is disposed between the examination subject and the cassette. A compression means may also be provided above the support plate.

In such conventional installations, the secondary radiation grid attenuates the secondary radiation emerging from the examination subject, however, has the disadvantage of increasing the distance between the subject and the film in the cassette. Additionally, in some instances it is preferable to make exposures without the use of a secondary radiation grid.

SUMMARY OF THE INVENTION

It is an object of the present invention to provide an X-ray diagnostic installation having a support plate with a secondary radiation grid which can be optionally positioned with the secondary radiation grid disposed in front of or behind the X-ray film cassette contained in the support plate.

The above object is inventively achieved in a support plate for an X-ray diagnostics installation which is mounted so as to be rotatable about an axis which is perpendicular to a central ray of the X-ray beam. The secondary radiation grid is disposed on one side or surface of the support plate, and the X-ray cassette is contained in a chamber with the secondary radiation grid overlying the chamber on one side. The support plate can be rotated so as to dispose the secondary radiation grid over or in front of the X-ray cassette in the direction of beam propogation, such that the secondary radiation grid is between the examination subject and the cassette, and can be rotated such that the secondary radiation grid is beneath or behind the cassette in the direction of beam propogation. X-ray exposures without the use of the secondary radiation grid can thus be produced in a simple manner by pivoting or rotating the support plate. The secondary radiation grid is relatively mechanically sensitive, and need not be removed from the support plate, as in conventional installations, in order to make this type of exposure.

In a further embodiment of the invention, a radiation detector for providing a signal to an automatic exposure control unit may be disposed at the side of the support plate facing away from the radiation grid. The radiation detector thus receiving the radiation dose following the X-ray film in the direction of beam propogation. When an X-ray film cassette is inserted into the chamber for exposure without the secondary radiation grid, in which case the support plate is rotated such that the secondary radiation grid is disposed behind the X-ray film cassette in the direction of beam propogation, the exposure time can also be controlled by the automatic exposure unit. If a specific side of the radiation detector must be exposed to the X-ray beam, the radiation detector may be mounted so as to be rotatable about an axis which is substantially parallel to the axis of revolution of the support plate, or is coincident therewith, so that the necessary side of the detector can be rotated so as to have the X-ray beam incident thereon.

DESCRIPTION OF THE PREFERRED EMBODIMENTS

Figure 1:
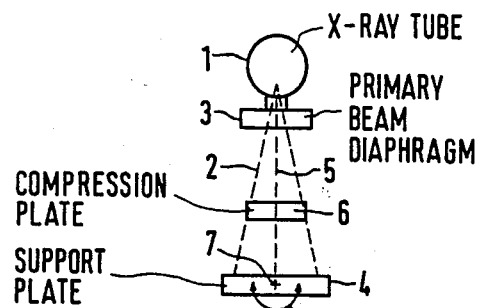
FIG. 1 is a side schematic view of an X-ray diagnostics installation constructed in accordance with the principles of the present invention.

An X-ray installation constructed in accordance with the principles of the present invention is schematically shown in FIG. 1 consisting of an X-ray tube 1 for generating an X-ray beam 2 which passes through a primary beam diaphragm 3. An exposure subject, such as the breast of a female patient to be examined, is supported on a support plate 4 and may be compressed by a compression plate 6 which is movable in the direction of a central ray 5 of the X-ray beam 2. The support plate 4 is rotatable about an axis 7, which is substantially perpendicular to the central ray 5, as indicated by the curved double arrow 8. The support plate 4 has a secondary radiation grid on one side thereof, described in greater detail below, and rotation of the support plate 4 permits the secondary radiation grid to be optionally positioned above or below a film cassette contained within the support plate 4.

Figure 2:
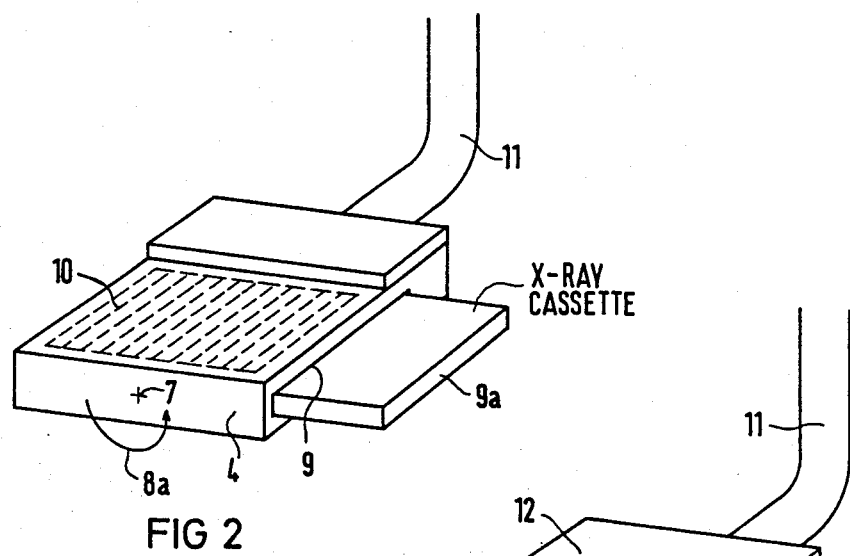
FIG. 2 is a perspective view of a support plate for an X-ray diagnostics installation constructed in accordance with the principles of the present invention in a first position.
Figure 3:
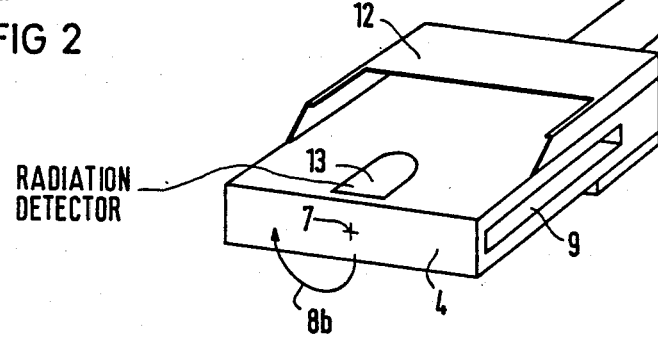
FIG. 3 is a perspective view of a support plate for an X-ray diagnostics installation constructed in accordance with the principles of the present invention rotated 180° from the position shown in FIG. 2 to a second position.

Further details of the support plate 4 are shown in FIGS. 2 and 3, which show the two exposure positions of the support plate 4. The support plate 4 has a lateral chamber or receptacle 9 for receiving an X-ray film cassette 9a. The support plate 4 has a secondary radiation grid 10 disposed on one side thereof. With the support plate 4 in the position shown in FIG. 2, the secondary radiation grid 10 is disposed in front of the exposure chamber 9, and thus in front of the film cassette therein, in the direction of beam propogation. The lamellae of the secondary radiation grid 10 are directed to the focus of the X-ray tube 1 and accordingly suppress radiation scatter proceeding from the exposure subject.

The support plate 4 is rotatably seated on an angled arm 11 so as to be pivotable about the axis 7. Pivoting the plate 4 in the direction of the arrow 8a shown in FIG. 2 places the plate 4 in the position shown in FIG. 3 wherein the secondary radiation grid 10 is disposed behind the chamber 9 as seen in the radiation direction. In order to decrease the distance between the examination subject and the X-ray film cassette, the X-ray film cassette may be inserted in a compartment 12 of the support plate 4, the compartment 12 being beneath the support plate 4 when the support plate 4 is in the position shown in FIG. 2. An X-ray exposure can thus be undertaken without the intervening secondary radiation grid 10. A minimum subject/film distance is accordingly achieved. Rotation of the support plate 4 in the direction of arrow 8b returns the support plate 4 to the position shown in FIG. 2.

The support plate 4 may, as shown in FIG. 3, be provided on the side thereof facing away from the secondary radiation grid 10 with a radiation detector 13. The radiation detector 13 may provide a signal to an automatic X-ray exposure control unit for automatically setting an optimum exposure time.

Radiation detectors such as the radiation detector 13 normally have one surface on which the radiation must be incident. Accordingly, in the embodiment shown in FIG. 4 the radiation detector 13 is mounted on an arm 14 having a gimbal joint 14a. The arm 14 and the radiation detector 13 are normally contained in a recess 15 in one side of the support plate 4. The joint 14a permits the radiation detector 13 to be moved in the direction of double arrow 21 to the position 13a indicated by dot and dashed lines. When in position 13a, the radiation detector 13 can then be rotated as indicated by the double arrow 16 to place the proper side of the radiation detector facing the radiation beam.

Figure 5:
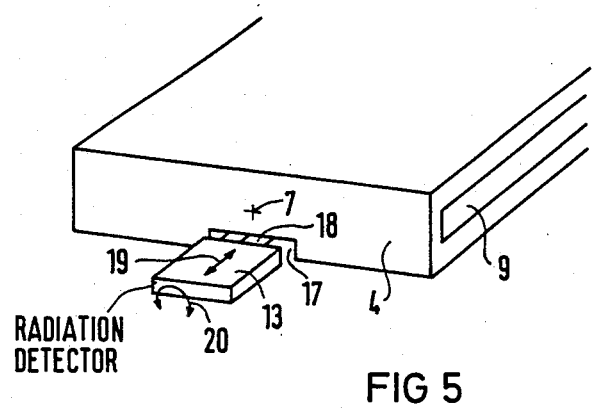
FIG. 5 is a perspective view of a further embodiment of a support plate for an X-ray diagnostics installation constructed in accordance with the principles of the present invention with a rotatable radiation detector.

A further embodiment of a support plate 4 constructed in accordance with the principles of the present invention is shown in FIG. 5, wherein the radiation detector 13 is disposed in a recess 17 on the side of the support plate facing away from the radiation grid 10. The radiation detector 13 is mounted on an arm 18 which permits the detector 13 to be withdrawn toward the front of the plate 4 as indicated by the double arrow 19. Once withdrawn, the radiation detector 13 can then be rotated as indicated by the curved double arrow 20 to place the appropriate side of the detector 13 such that the X-radiation is incident thereon. The radiation detector 13 is then reinserted in the receptacle 17. It is also possible to expose the radiation detector 13 by moving the plate 4, instead of the detector 13.

Figure 4:
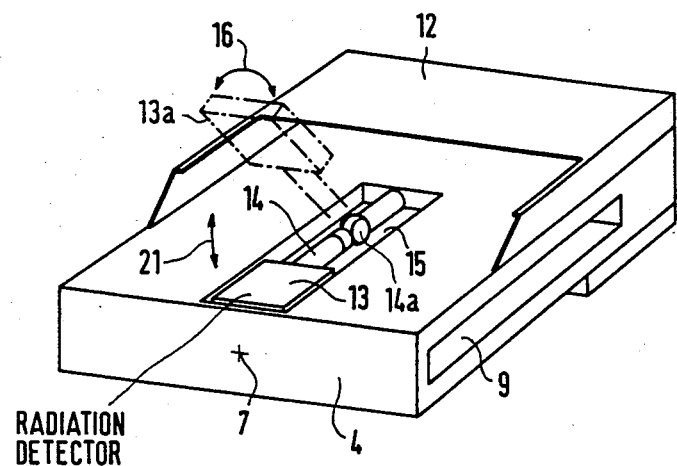
FIG. 4 is a perspective view of a support plate for an X-ray diagnostics installation constructed in accordance with the principles of the present invention having a rotatable radiation detector.

FIG. 4 shows the support plate 4 positioned for generating an exposure without the use of the secondary radiation grid, corresponding to that shown in FIG. 3. FIG. 5 shows the plate 4 positioned for obtaining an exposure with the secondary radiation grid 10, corresponding to FIG. 2.

The exposure chamber 9 in the support plate 4 accepts a standard X-ray film cassette having dimensions, for example, of approximately 24×30 cm. A slightly larger cassette can be accommodated in the compartment 12. The support plate 4 may be dimensioned such that a cassette inserted into the compartment 12 projects slightly beyond the front edge of the support plate 4. By so doing, the approach of the cassette to the exposure subject is not impeded by the support plate 4, that is, the edge of the film cassette can be placed directly against the thorax of the patient so that the exposure subject is completely imaged on the X-ray film.

Although modifications and changes may be suggested by those skilled in the art it is the intention of the inventor to embody within the patent warranted hereon all changes and modifications as reasonably and properly come within the scope of his contribution to the art.

I claim as my invention:

1. An X-ray transparent support plate in combination with an X-ray diagnostics installation having means for generating an X-ray beam, a secondary radiation grid disposed on one side of said plate, an exposure chamber for receiving an X-ray film cassette on the other side of said plate, and a means for rotatably mounting said support plate for pivoting said support plate about an axis which is substantially perpendicular to a central ray of said X-ray beam, such that said support plate can be optionally positioned with said secondary radiation grid disposed in front of or behind said X-ray film cassette in the direction of propogation of said X-ray beam.

2. A support plate as claimed in claim 1 further comprising a radiation detector disposed in a receptacle in a side of said support plate facing away from the side of said support plate at which said secondary radiation grid is disposed, and a means for mounting said radiation detector permitting withdrawal of said radiation detector from said recess for positioning a selected side of said radiation detector facing said radiation beam.

3. A support plate as claimed in claim 2 wherein said means for mounting said radiation detector consists of an arm having a gimbal joint permitting said radiation detector to be raised from said recess and rotated outside said recess.

4. A support plate as claimed in claim 3 wherein said arm has a portion, interconnected between said gimbal joint and said radiation detector, movable in a plane defined by said central ray of said beam and the axis of rotation of said support plate.

5. A support plate as claimed in claim 3 wherein said means for mounting said radiation detector consists of an arm permitting relative lateral displacement of said radiation detector relative to said support plate along an axis substantially parallel to the axis of rotation of said support plate.

6. An X-ray diagnostics installation comprising:
   an X-ray tube for generating an X-ray beam having a central ray;
   an X-ray transparent support plate disposed within said X-ray beam for supporting an examination subject and having a secondary radiation grid on one side of the plate and a receptacle for receiving an X-ray film cassette on the other side of said plate; and
   a means for rotatably mounting said support plate permitting pivoting of said support plate about an axis of rotation which is substantially perpendicular to said central ray such that said support plate can be optionally positioned with said secondary radiation grid disposed above or below an X-ray film cassette received in said chamber in the direction of radiation propogation.

7. An X-ray diagnostics installation as claimed in claim 6 wherein said support plate further comprises a radiation detector disposed in a receptacle in a side of said support plate facing away from the side of said support plate at which said secondary radiation grid is disposed, and a means for mounting said radiation detector permitting withdrawal of said radiation detector from said recess for positioning a selected side of said radiation detector facing said radiation beam.

8. A support plate as claimed in claim 7 wherein said means for mounting said radiation detector consists of an arm having a gimbal joint permitting said radiation detector to be raised from said recess and rotated outside said recess.

9. A support plate as claimed in claim 8 wherein said arm has a portion, interconnected between said gimbal joint and said radiation detector, movable in a plane defined by said central ray of said beam and the axis of rotation of said support plate.

10. A support plate as claimed in claim 8 wherein said means for mounting said radiation detector consists of an arm permitting relative lateral displacement of said radiation detector relative to said support plate along an axis substantially parallel to the axis of rotation of said support plate.

* * * * *